US00PP12385P2

(12) United States Plant Patent
Utecht

(10) Patent No.: US PP12,385 P2
(45) Date of Patent: Feb. 5, 2002

(54) GERANIUM PLANT NAMED 'FISCHERRY'

(75) Inventor: Angelika Utecht, Montabaur (DE)

(73) Assignee: Foley & Lardner, Binningen (CH)

( * ) Notice: Subject to any disclaimer, the term of this patent is extended or adjusted under 35 U.S.C. 154(b) by 0 days.

(21) Appl. No.: 09/631,661

(22) Filed: Aug. 3, 2000

(51) Int. Cl.[7] ..... A01H 5/00
(52) U.S. Cl. ..... Plt./332
(58) Field of Search ..... Plt./332, 324

*Primary Examiner*—Bruce R. Campell
*Assistant Examiner*—Kent L. Bell
(74) *Attorney, Agent, or Firm*—Foley & Lardner

(57) ABSTRACT

A new and distinct cultivar of geranium plant named 'Fischerry', as described and illustrated, and particularly characterized by the combined features of light-red to cherry-red flower color; numerous compact inflorescences; light, medium green, slightly zoned foliage; medium-tall; well-branched; round, only semi-trailing plant habit; and early spring flowering response.

1 Drawing Sheet

BACKGROUND OF THE INVENTION

The present invention relates to a new and distinct cultivar of geranium plant, botanically known as *Pelargonium peltatum*, and hereinafter referred to by the cultivar name 'Fischerry'.

'Fischerry' is a product of a planned breeding program which had the objective of creating ivy-leafed geranium varieties with reddish flower color and double, many petalled flower form, in combination with moderately vigorous growth and fair weather resistance.

'Fischerry' originated from a hybridization made by the inventor, Angelika Utecht, in a controlled breeding program in Galdar, Gran Canaria, Spain, in 1995. The female parent was the variety 'Fischerry' (U.S. Plant Pat. No. 10,365), characterized by dark-red, double flowers, relatively dark-green foliage and medium plant habit. The male parent was the variety 'Nanette' (U.S. Plant Pat. No. 7,360; commercially known as 'Gauguin', which is the original name used in Europe), characterized by oranged-red, semi-double flowers, fresh-green foliage with slight zonation, and moderately vigorous growth.

'Fischerry' was selected as one flowering plant within the progeny of the stated cross by the inventor, Angelika Utecht, in 1996 in a controlled environment in Galdar, Gran Canaria, Spain.

The first act of asexual reproduction of 'Fischerry' was accomplished when vegetative cuttings were taken from the initial selection in autumn 1996 in a controlled environment in Galdar, Gran Canaria, Spain, by, or under the supervision of, Angelika Utecht. Horticultural examination of plants grown from cuttings of the plant, initiated in May 1997 in Hillscheid, Germany, and continuing thereafter, has demonstrated that the combination of characteristics as herein disclosed for 'Fischerry' are firmly fixed and are retained through successive generations of asexual reproduction.

BRIEF DESCRIPTION OF THE INVENTION

The following traits have been repeatedly observed and are determined to be basic characteristics of 'Fischerry', which in combination distinguish this geranium as a new and distinct cultivar:

1. Light-red to cherry-red, many-petalled flowers;
2. Compact, small to medium sized umbels;
3. Rose-bud shape of buds;
4. Medium-green foliage with weak zonation;
5. Medium (mid-season) spring flowering response and rich flowering throughout the summer; and
6. Medium tall, semi-trailing plant habit.

'Fischerry' has not been observed under all possible environmental conditions. The phenotype of the new cultivar may vary significantly with variations in environment such as temperature, light intensity and day length without and change in the genotype. The following observations, measurements, and comparisons describe plants grown in Hillscheid, Germany, under greenhouse conditions which approximate those generally used in commercial practice.

Of the many commercial cultivars known to the present inventor, the most similar in comparison to 'Fischerry' are the unpatented commercial variety 'Bernardo', which is registered as 'Guiber' for a Plant Breeder's Rights application in Europe, and the unpatented variety 'Fisberi'. In comparison to 'Bernardo', 'Fischerry' has a similar flower color and flower type, but somewhat larger inflorescences, weakly zoned foliage in comparison to the foliage of 'Bernardo' which is without zonation, and more vigorous growth.

In comparison to 'Fisberi', 'Fischerry' has a slightly more scarlet, less bluish shade of flower color with less tendency to fading, somewhat larger umbels, lighter, more grass-green colored foliage with distinct zonation, and a more bushy, round, semi-trailing plant habit.

BRIEF DESCRIPTION OF THE DRAWING

The accompanying photographic illustration showns typical flower and foliage characteristics of 'Fischerry' with colors being as true as possible with an illustration of this type.

DETAILED BOTANICAL DESCRIPTION

The measurements were taken in Hillscheid, Germany, on May 10, 2000, 13 weeks after planting of rooted cuttings into 14-cm pots. The plants had been pinched. In the following description, color references are made to The Royal Horticultural Society (R.H.S.) Colour Chart. The color values were determined indoors from plants developed in a greenhouse in May 2000 in Hillscheid, Germany.

Classification:

*Botanical*.—A hybrid of the species *Pelargonium peltatum.*

*Commercial*.—Ivy geranium, cv. 'Fischerry'.

Inflorescence:

*Umbel*.—Shape: Semi-spherical. Average diameter: 78 mm. Average depth: 45 mm. Peduncle length: 145 mm. Peduncle color: Green, RHS 143 B. Pedicel length: 20 mm. Pedicel color: Green, RHS 143 B, slight infusion of anthocyanin at the upper end, reddish-brown RHS 179 B. Number of flowers per umbel: 11.4. Lastingness of the umbel: Approximately 14 days.

*Corolla*.—Average diameter: 50 mm. Form: Double, many petalled. Shape: Oval, with the two upper petals longer than the rest, rose-bud shape when unfolding (opening). Petal Size: 2 upper petals are 34–34 mm long, 14–16 mm wide; petals of the basal layer are approximately 28 mm long, 14 mm wide (petals diminish in size towards the middle of the flower). Petal Shape: Spatulate or oblong, with the upper end rounded or weakly lobate; attenuate base, margin entire. Number of petals: 25 on average. Color (general tonality from a distance of 3 meters): Carmine to light red. Color of upper petals: Upper surface, RHS 46 C. Makings of upper petals: Two violet veins, RHS 74 A, and a small dot, RHS 74 A, surrounding a light pink stripe, RHS 55 C or lighter, these markings are usually covered by the inner petals. Color of lower petals: Upper surface, more intense but closest to RHS 52 A; as flower matures, there is a trace of RHS 57 B. Color of lower surface of petals: RHS 46 C, for both upper and lower petals. Number of petaloids: 3–5 . Color of petaloids: Upper surface, RHS 46 C; lower surface, RHS 46 D. Color of sepals: Visible outward color is light green, RHS 143 B, the inner, upper surface (usually not visible as covered by petals) is approximately RHS 143 C. Number of sepals: 6–7. Sepal Size: 14–15 mm long; 0.4 mm wide for the largest upper sepal, 2–3 mm for the other sepals.

*Bud* (*immediately before unfolding of the petals*).—Shape: Elliptical. Color (sepals): Light-green, RHS 143 B. Color (petals): Color range from red to light red, RHS 46 C–RHS 46 D, marbled. Length: 20 mm. Width: 11 mm.

*Reproductive organs*.—Androecium: Absent, or only few, infertile anthers or petaloids. Gynoecium: 1–2 pistils, pink stigma and filament. Fertility/seed set: No seed set observed.

*Spring flowering response period*.—In Hillscheid, Germany, in 1999, plants had on average 0.8 flowers opened 12 weeks after planting of unrooted cuttings.

*Outdoor flower production*.—Floriferous, numerous, relatively small inflorescences; the flower count in 1999, in Hillscheid, Germany, indicated about 7–8 inflorescences per plant for mid-May.

*Durability*.—Good shatter resistance, fair rain resistance for a double-flowered variety and good stability of flower color (little fading).

*Lastingness of the individual bloom*.8–9 days at approximately 18° C. in spring.

*Fragrance*.—None.

Plant:

*Foliage*.—Form: Ivy-shape with distinct lobes. Margin: Entire. Size of leaf: 78 mm wide; 44 mm long. Color of upper surface: Green, coloration between RHS 137 D and RHS 143 A (slightly glossy); lower surface is RHS 137 D (dull). Color of zonation: Brown, about RHS 166 A, weak to medium, only weak in summer. Tolerance of botrytis: Average. Leaf Petiole: Aproximately 6–8 cm; diameter 2–3 mm; light green color, RHS 143 C.

*General appearance and form*.—Internode length: 30–40 mm. Branching pattern: 9 branches. Size of plant/length of branches: 25 cm as measured from the base of the main stem to the tips of the branches (12 weeks after planting), 60–65 cm (in early September, 30 weeks after planting).

I claim:

1. A new and distinct cultivar of geranium plant named 'Fischerry', as described and illustrated.

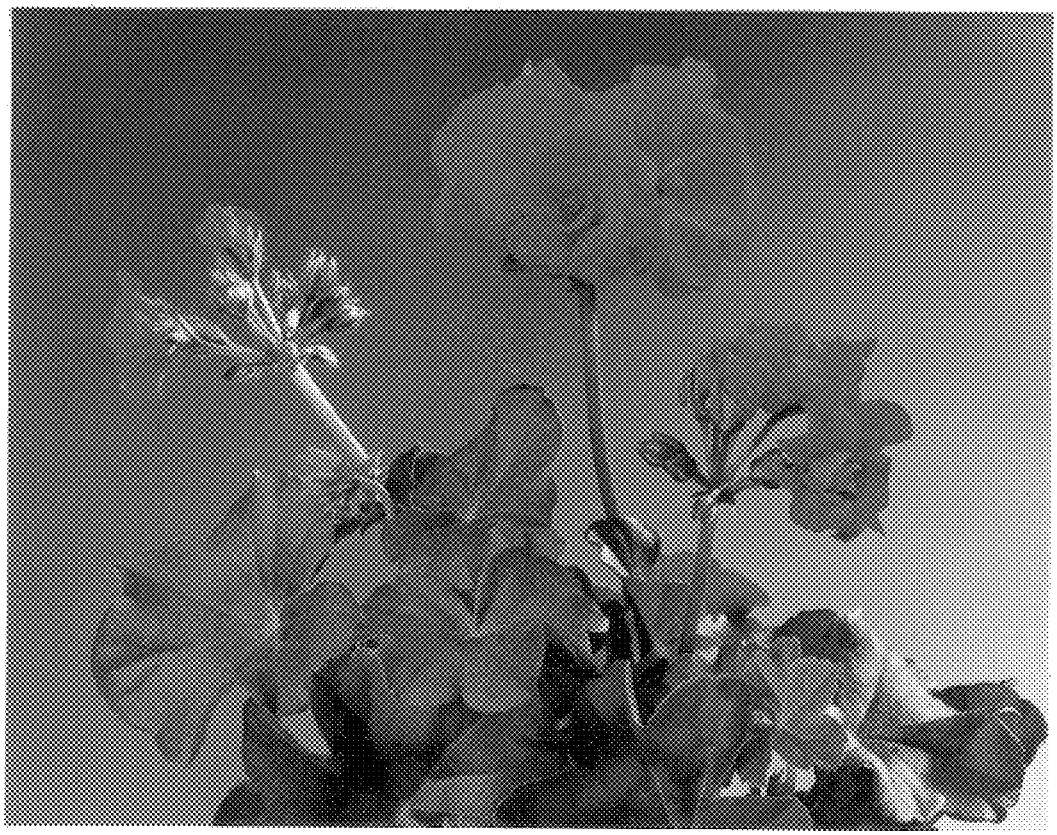

* * * * *